US007771467B2

(12) United States Patent
Svensson

(10) Patent No.: US 7,771,467 B2
(45) Date of Patent: Aug. 10, 2010

(54) APPARATUS FOR REPAIRING THE FUNCTION OF A NATIVE AORTIC VALVE

(75) Inventor: Lars G. Svensson, Gates Mills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 255 days.

(21) Appl. No.: 11/923,405

(22) Filed: Oct. 24, 2007

(65) Prior Publication Data

US 2008/0275548 A1 Nov. 6, 2008

Related U.S. Application Data

(60) Provisional application No. 60/856,428, filed on Nov. 3, 2006.

(51) Int. Cl.
*A61F 2/06* (2006.01)
*A61F 2/24* (2006.01)

(52) U.S. Cl. ............... 623/1.26; 623/2.14; 623/2.18; 623/1.24

(58) Field of Classification Search ............... 623/1.24, 623/1.26, 2.12, 2.13, 2.18, 1.35, 2.1, 2.14
See application file for complete search history.

(56) References Cited

U.S. PATENT DOCUMENTS

| 5,178,634 | A | | 1/1993 | Ramos Martinez | |
|---|---|---|---|---|---|
| 5,314,468 | A | | 5/1994 | Ramos Martinez | |
| 5,891,195 | A | | 4/1999 | Klostermeyer et al. | |
| 5,957,949 | A | | 9/1999 | Leonhardt et al. | |
| 5,984,955 | A | * | 11/1999 | Wisselink | 623/1.35 |
| 6,110,201 | A | * | 8/2000 | Quijano et al. | 623/2.1 |
| 6,129,756 | A | * | 10/2000 | Kugler et al. | 623/1.27 |
| 6,344,056 | B1 | * | 2/2002 | Dehdashtian | 623/1.35 |
| 6,524,336 | B1 | * | 2/2003 | Papazolgou et al. | 623/1.35 |
| 6,814,752 | B1 | * | 11/2004 | Chuter | 623/1.35 |

(Continued)

FOREIGN PATENT DOCUMENTS

WO    WO 2004/034933 A2    4/2004

(Continued)

*Primary Examiner*—Alvin J Stewart
(74) *Attorney, Agent, or Firm*—Tarolli, Sundheim, Covell & Tummino LLP

(57) ABSTRACT

An apparatus for repairing the function of a native aortic valve, defining a native valve annulus, of a patient includes a tubular valve support member having oppositely disposed first and second valve member ends and a valve member body located between the first and second valve member ends. The valve support member defines a longitudinal axis. A prosthetic valve has at least two prosthetic valve leaflets that are coaptable to permit the unidirectional flow of blood. The prosthetic valve is attached to the valve support member adjacent the second valve member end. At least two coronary openings in the valve member body are located longitudinally adjacent free edges of the at least two prosthetic valve leaflets. At least one of the coronary openings is located so as to be selectively radially aligned with a coronary ostium when the prosthetic valve is located substantially within the native valve annulus. At least two branch support members are provided, with each branch support member having first and second branch ends. Each first branch end is attachable to a coronary opening with the second branch end extending radially away from the valve support member and through a coronary ostium.

11 Claims, 3 Drawing Sheets

U.S. PATENT DOCUMENTS

| | | | |
|---|---|---|---|
| 7,018,404 B2 * | 3/2006 | Holmberg et al. | 623/1.26 |
| 7,022,134 B1 * | 4/2006 | Quijano et al. | 623/1.24 |
| 7,195,641 B2 * | 3/2007 | Palmaz et al. | 623/2.18 |
| 7,201,772 B2 * | 4/2007 | Schwammenthal et al. | 623/2.18 |
| 7,261,732 B2 * | 8/2007 | Justino | 623/1.24 |
| 7,306,623 B2 * | 12/2007 | Watson | 623/1.16 |
| 7,377,938 B2 * | 5/2008 | Sarac et al. | 623/1.26 |
| 7,510,574 B2 * | 3/2009 | L et al. | 623/2.14 |
| 2002/0156523 A1 | 10/2002 | Lau et al. | |
| 2002/0193871 A1 * | 12/2002 | Beyersdorf et al. | 623/1.26 |
| 2003/0023303 A1 | 1/2003 | Palmaz et al. | |
| 2003/0130720 A1 * | 7/2003 | DePalma et al. | 623/1.13 |
| 2004/0236411 A1 | 11/2004 | Sarac et al. | |
| 2004/0260389 A1 | 12/2004 | Case et al. | |
| 2005/0043790 A1 | 2/2005 | Seguin | |
| 2005/0096736 A1 | 5/2005 | Osse et al. | |
| 2005/0102018 A1 * | 5/2005 | Carpenter et al. | 623/1.11 |
| 2006/0178733 A1 * | 8/2006 | Pinchuk et al. | 623/1.35 |
| 2006/0229707 A1 * | 10/2006 | Khoury | 623/1.16 |
| 2008/0312732 A1 * | 12/2008 | Hartley et al. | 623/1.13 |

FOREIGN PATENT DOCUMENTS

| | | |
|---|---|---|
| WO | WO 2004/034933 A3 | 4/2004 |
| WO | WO 2004/093935 A2 | 11/2004 |

* cited by examiner

APPARATUS FOR REPAIRING THE FUNCTION OF A NATIVE AORTIC VALVE

RELATED APPLICATION

This application claims priority from U.S. provisional patent application Ser. No. 60/856,428, filed on Nov. 3, 2006, the subject matter of which is incorporated herein by reference.

TECHNICAL FIELD

The present invention relates to an apparatus for repairing the function of a native aortic valve and, more particularly, to such an apparatus having at least one branch support member.

BACKGROUND OF THE INVENTION

It is known to implant prosthetic valves in various body passages to replace native valves that are diseased or otherwise defective in some manner. Blood pressure, as provided by heart activity via the arteries, is normally sufficient to maintain the flow of blood in one direction through the vasculature. The blood pressure in the veins is much lower than in the arteries and venous valves function to limit the backflow of blood through the veins. Numerous such venous valves are located throughout the venous system and are particularly important to maintaining directional blood flow in the lower extremities.

Another common type of prosthetic valve is a prosthetic cardiac valve. Prosthetic cardiac valves have been used to replace all four of the native cardiac valves. Cardiac valve replacement has traditionally been done though an invasive open surgical procedure, although endovascular (or percutaneous) approaches are being developed.

The four native cardiac valves (mitral, aortic, tricuspid, and pulmonary) serve to direct the flow of blood through the two sides of the heart in a forward direction. On the left (systemic) side of the heart, the mitral valve is located between the left atrium and the left ventricle, while the aortic valve is located between the left ventricle and the aorta. These two valves direct oxygenated blood coming from the lungs, through the left side of the heart, into the aorta for distribution to the body. On the right (pulmonary) side of the heart, the tricuspid valve is located between the right atrium and the right ventricle, while the pulmonary valve is located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these native cardiac valves are passive structures that do not themselves expend any energy and do not perform any active contractile function. The valves consist of moveable leaflets that open and close in response to differential pressures on either side of the valve. The mitral and tricuspid valves are referred to as atrioventricular valves because they are situated between an atrium and a ventricle on each side of the heart. The mitral valve has two leaflets and the tricuspid valve has three leaflets. The aortic and pulmonary valves are referred to as semilunar valves because of the unique appearance of their leaflets, which are often termed "cusps" and which are shaped somewhat like a half-moon. The aortic and pulmonary valves each have three cusps.

Cardiac valves can exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

The two major problems that can develop with cardiac valves are stenosis, in which a valve does not open properly, and insufficiency (also called regurgitation), in which a valve does not close properly. Stenosis and insufficiency may occur concomitantly in the same valve or in different valves. Both of these abnormalities increase the workload and stress placed on the heart. The severity of this increased stress on the heart, and the heart's ability to adapt to it, determine whether the abnormal valve will have to be surgically repaired or replaced.

In addition to stenosis and insufficiency of cardiac valves, surgery may also be required for certain types of bacterial or fungal infections in which the valve may continue to function normally, but nevertheless harbors an overgrowth of bacteria on the leaflets of the valve that may flake off (or embolize) and lodge downstream in a vital artery. If this occurs on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or the aortic valve may be necessary for this problem even though neither stenosis nor insufficiency of either valve is present.

If a cardiac valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include mechanical valves, tissue valves, and homograft valves.

Mechanical valves include caged-ball valves, bi-leaflet valves, and tilting disk valves. The main advantage of mechanical valves is their long-term durability. Their main disadvantage is that they require the patient to take systemic anticoagulation drugs for the rest of his or her life, because of the propensity of mechanical valves to cause blood clots to form on them.

Tissue valves are typically constructed either by sewing the leaflets of porcine aortic valves to a stent (to hold the leaflets in proper position), or by constructing valve leaflets from porcine or bovine pericardial tissue and sewing them to a stent. The stents may be rigid or slightly flexible and are typically covered with a fabric, such as the material sold under the trademark Dacron®, and then attached to a sewing ring for fixation to the patient's native valve annulus. The porcine or bovine tissue is chemically treated to alleviate any antigenicity (i.e., to reduce the risk that the patient's body will reject the foreign tissue). Tissue valves may be used to replace any of the heart's four valves. The main advantage of tissue valves is that they do not cause blood clots to form as readily as do the mechanical valves, and therefore, they do not necessarily require systemic anticoagulation.

Homograft valves are harvested from human cadavers. Homograft valves are rarely used, except for treating endocarditis. The main disadvantage of these valves is that they are not available in sufficient numbers to satisfy the needs of patients who need new aortic or pulmonary valves. Homograft valves are also extremely expensive and can be more difficult to implant, and less durable, than either mechanical valves or tissue valves.

Replacement of a native aortic valve may provide particular difficulties. The aortic valve controls the flow of blood to the ascending aorta. The coronary arteries are the only branches of the ascending aorta, supplying blood to all structures within the pericardial cavity. There are two coronary artery ostia, or openings, with each ostium being located in the center of one of the left and right (coronary) sinuses of the aortic valve. The coronary ostia need to remain unobstructed following a valve replacement surgery, in order to maintain a fluid connection between the ascending aorta and the coronary arteries. However, the graft and/or stent supporting the replacement aortic valve tends to at least partially obstruct the coronary ostia, leading to undesirable results. In the known David's valve-sparing aortic root replacement surgical method, maintenance of the coronary ostia fluid connection is attempted by creating openings in the graft after implantation, then suturing the coronary arteries to these openings. However, this technique may be time-consuming and/or result in at least a partial obstruction of the coronary ostia by the sutures or scar tissue formation.

In addition, cardiac valve replacement using any of the aforementioned prostheses has traditionally been done via an open surgical technique in which the thoracic cavity is opened. This exacting operation requires use of a heart-lung machine for external circulation of the blood as the heart is stopped and opened during the surgical intervention and the artificial cardiac valve is implanted under direct vision. This operation exposes the patient to many risks especially in the elderly population. Hence, an apparatus for repairing the function of a diseased cardiac valve via an endovascular (or percutaneous) procedure, rather than an open surgical procedure, could offer tremendous benefits for these patients, many of whom have no options today. In addition, such an apparatus which allows for preservation of the coronary ostia and the associated fluid connection could also lead to a beneficial result in many patients.

SUMMARY OF THE INVENTION

In an embodiment of the present invention, an apparatus for repairing the function of a native aortic valve of a patient is described. The native aortic valve defines a native valve annulus. The apparatus includes a tubular valve support member having oppositely disposed first and second valve member ends and a valve member body located between the first and second valve member ends. The valve support member defines a longitudinal axis. A prosthetic valve has at least two prosthetic valve leaflets that are coaptable to permit the unidirectional flow of blood. The prosthetic valve is attached to the valve support member adjacent the second valve member end. At least two coronary openings in the valve member body are located longitudinally adjacent free edges of the at least two prosthetic valve leaflets. At least one of the coronary openings is located so as to be selectively radially aligned with a coronary ostium when the prosthetic valve is located substantially within the native valve annulus. At least two branch support members are provided, with each branch support member having first and second branch ends. Each first branch end is attachable to a coronary opening with the second branch end extending radially away from the valve support member and through a coronary ostium.

BRIEF DESCRIPTION OF THE DRAWINGS

For a better understanding of the invention, reference may be made to the accompanying drawings, in which.

DESCRIPTION OF EMBODIMENTS

Figure 1:
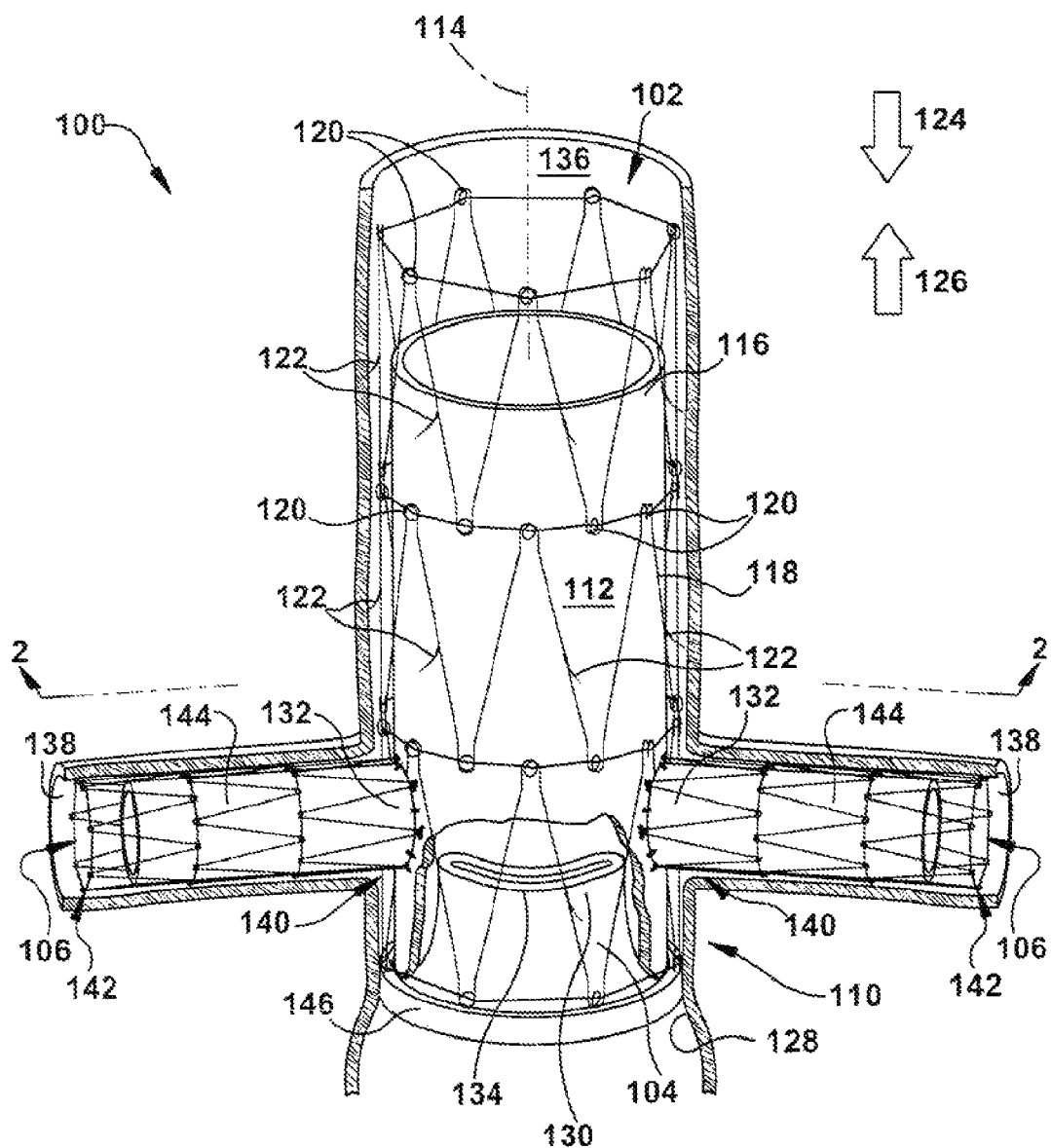
FIG. 1 is a side view of one embodiment of the present invention.

In accordance with the present invention, FIG. 1 depicts an apparatus 100 for repairing the function of a native cardiac valve, discussed herein as being a native aortic valve, of a patient. It should be apparent, however, to those skilled in the art that the apparatus 100 disclosed herein can also be used to repair the function of other cardiac valves, as well as venous valves. The apparatus 100 includes a tubular valve support member 102, a prosthetic valve 104, and two branch support members 106.

The valve support member 102 may be a self-expanding or balloon expandable stent made from stainless steel, but could alternatively be made from any suitable medical grade plastic or metal, including shape memory metals such as Nitinol. The valve support member 102 has oppositely disposed first and second valve member ends 108 and 110, respectively, separated by a valve member body 112. The valve support member 102 has a longitudinal axis 114 and may be at least partially lined with a valve support member graft 116.

The valve member body 112 may be made up of a plurality of axially extending beams 118 having a known "M" or "Z" shape. These beams 118, or another structure of the valve support member 102, define generally cylindrical inner and outer surfaces (not numbered) for the valve support member 102.

The valve support member 102 may include a plurality of eyelets 120 located at any suitable positions on the valve support member. The valve support member 102 may also include a plurality of hooks, barbs, or other anchor members 122 located on the outer surface of the beams 118. The anchor members 122, when present, extend radially outward and at an angle to prevent migration of the valve support member 102 upon implantation. More specifically, the anchor members 122 may resist movement of the apparatus 100 in a first longitudinal direction 124 within a blood vessel of the patient and/or in a second longitudinal direction 126, opposite the first longitudinal direction. It should be understood that the location, quantity, configuration, and orientation of the anchor members 122 may be altered depending on specific needs of the apparatus 100.

To enhance the biocompatibility of the apparatus 100, it is contemplated that at least a portion of the valve support member 102 may be coated with a therapeutic agent such as, for example, an anti-coagulant, an anti-thrombogenic agent, an anti-proliferative agent, an anti-inflammatory agent, an antibiotic, an angiogenesis agent, a statin, a growth factor, or stem cells. The therapeutic agent may be loaded into a compound or polymer that is coated onto the valve support member 102 for a time-delayed release into surrounding tissue.

In addition, it should be noted that radiopaque markers may be attached at various locations on valve support member 102, and/or branch support members 106 to aid with placement of the apparatus 100 under fluoroscopy.

The valve support member graft 116 may be made of a biocompatible material such as Dacron®, woven velour, polyurethane, PTFE, or heparin-coated fabric. Alternatively, the valve support member graft 116 may be a biological material such as bovine or equine pericardium, a homograft, an autograft, or cell-seeded tissue, or of any other suitable material. The valve support member graft 116 may partially or wholly line the valve support member 102. The valve support member graft 116 may be attached to the valve support member 102 in any suitable manner, such as by suturing to the eyelets 120 or another structure of the valve support member, or by being woven to the first and/or second valve member end 108 or 110, for example.

The prosthetic valve 104 may be a homograft, an autograft, or made from a harvested biological material including, but not limited to, bovine pericardial tissue, equine pericardial tissue or porcine pericardial tissue. Alternatively, the prosthetic valve 104 may be made from a biocompatible synthetic material including, but not limited to, polyurethane or expanded PTFE.

The native aortic valve (not shown) defines a native valve annulus 128. The prosthetic valve 104 is attached, by sutures or other suitable means, to the valve support member 102 adjacent the second valve member end 110 so that the valve is suspended inside the native valve annulus 128. In the illustrated embodiments, the valve support member graft 116 has been broken away to show the bioprosthetic valve 104 as having two prosthetic valve leaflets 130 that are coaptable to permit the unidirectional flow of blood. However, it should be understood that the prosthetic valve 104 could have less than two or more than two leaflets 130.

The valve support member 102 includes at least one, but discussed herein as having two, coronary openings 132 in the valve member body 112. The coronary openings 132 may simply be interstitial spaces between the beams 118 or other structures of the valve support member 102. When the valve support member 102 is lined in the vicinity of the desired coronary openings 132, the valve support member graft 116 may include a coronary opening 132 as an aperture therethrough.

The coronary openings 132 are preferably located longitudinally adjacent free edges 134 of the prosthetic valve leaflets 130. At least one of the coronary openings 132 should be located so as to be selectively radially aligned with a coronary ostium 136 when the prosthetic valve 104 is located substantially within the native valve annulus 128. Thus, fluid communication can be established between the interior of the valve support member 102 in the ascending aorta 136 and the coronary arteries 138.

It is often desirable, however, for the fluid path between the valve support member 102 and the coronary arteries 138 to be reinforced and supported. The apparatus 100 therefore includes at least one branch support member 106, and preferably one branch support member for each coronary ostium 136.

The branch support members 106 each have first and second branch ends 140 and 142, respectively. The branch support members 106 and valve support member 102 may have similar or different structures. The branch support members 106 may each be at least partially lined with a branch support member graft 144. The branch member support grafts 144, like the valve support member graft 116, may be made of any suitable biocompatible or biological material, may line all or any portion of the branch support member 106, and may be attached to the branch support members 106 in any suitable manner.

The first branch ends 140 are each attachable to a coronary opening 132 of the valve support member 102 with the second branch ends 142 extending radially away from the valve support member and through a coronary ostium, thus positioning the branch support members 106 at least partially within the coronary arteries 138. Optionally, at least one branch support member 106 may extend away from the valve support member 102 in a direction perpendicular to the longitudinal axis 114.

Figure 2:
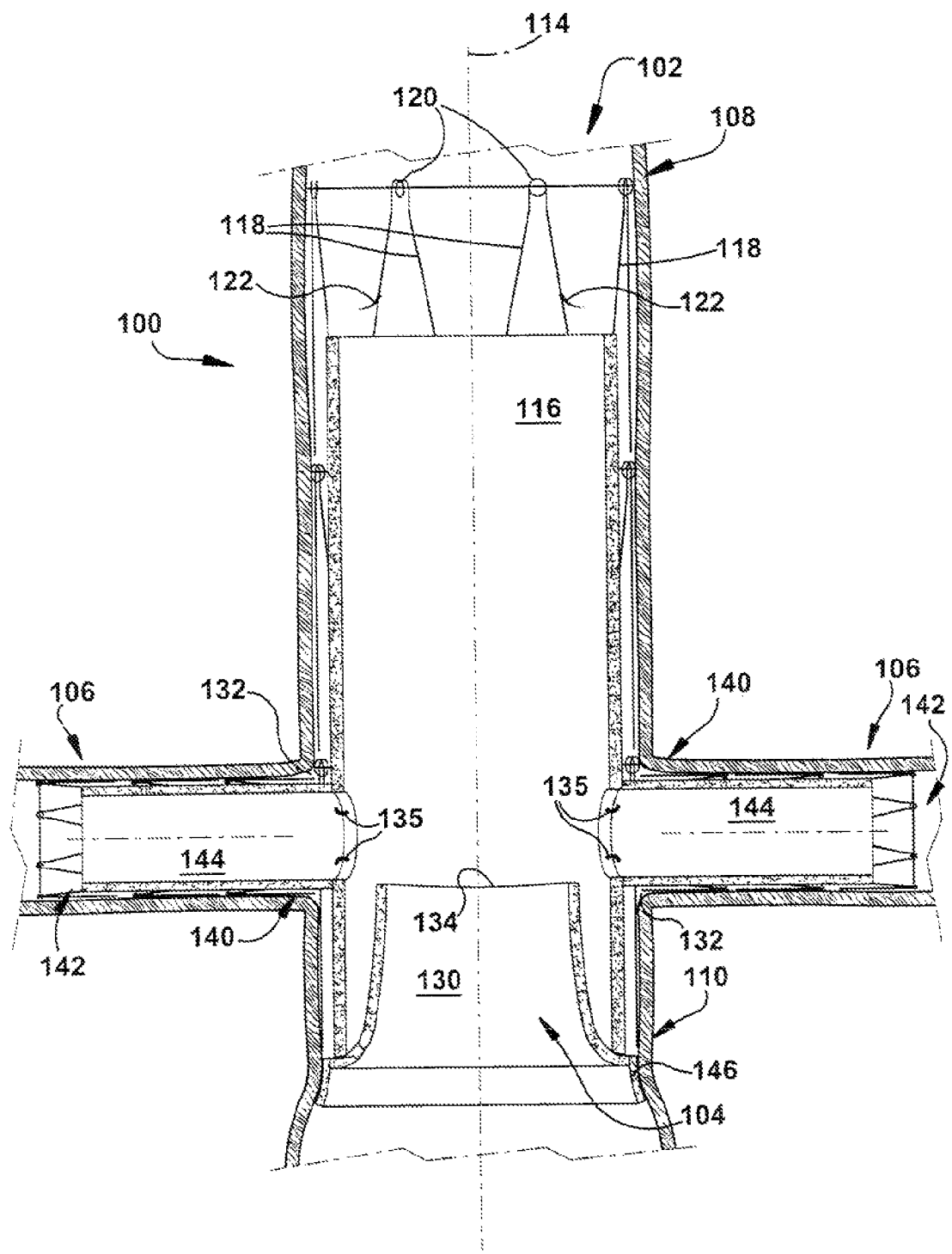
FIG. 2 is a cross-sectional view taken along line 2-2 of FIG. 1.

The branch support members 106 may be formed integrally with the valve support member 102 during manufacture or may be attached to the valve support member, such as through the sutures 135 shown in FIG. 2, after the valve support member has been manufactured. If the latter, at least one branch support member 106 may be attached to the valve support member 106 after the valve support member has been placed into a blood vessel, such as the ascending aorta 136, of the patient. In this manner, the relative sizes and locations of the valve support member 102 and the branch support members 106 may be customized to fit the anatomy of each patient individually.

Optionally, a cushioned cuff 146 may be attached to at least one of the first valve member end 108, the second valve member end 110 and the second branch end 142. Such a cuff 146 may help avoid frictional or compressive damage to the patient's vasculature, particularly to the native valve annulus 128, from the terminal portions of the apparatus.

One application for the present invention is to repair the function of a diseased native aortic valve. To enable delivery and deployment of the apparatus 100, the apparatus is radially collapsed and loaded into a sheath (not shown) over a catheter (not shown). After de-airing of the assembly, the apparatus 100 is delivered into the patient's vascular system in any desired manner. For example, the apparatus 100 may be delivered through an arteriotomy in one of the femoral, subclavian, or axillary arteries or the left ventricular apex. The apparatus 100 may instead be delivered via a venotomy, particularly when used in conjunction with a pulmonary valve. In the application of the apparatus 100 illustrated in FIGS. 1, 2, and 3, the apparatus may be delivered to a desired location in the ascending aorta just above the left ventricle under fluoroscopic and/or transesophageal echocardiographic guidance.

Figure 3:
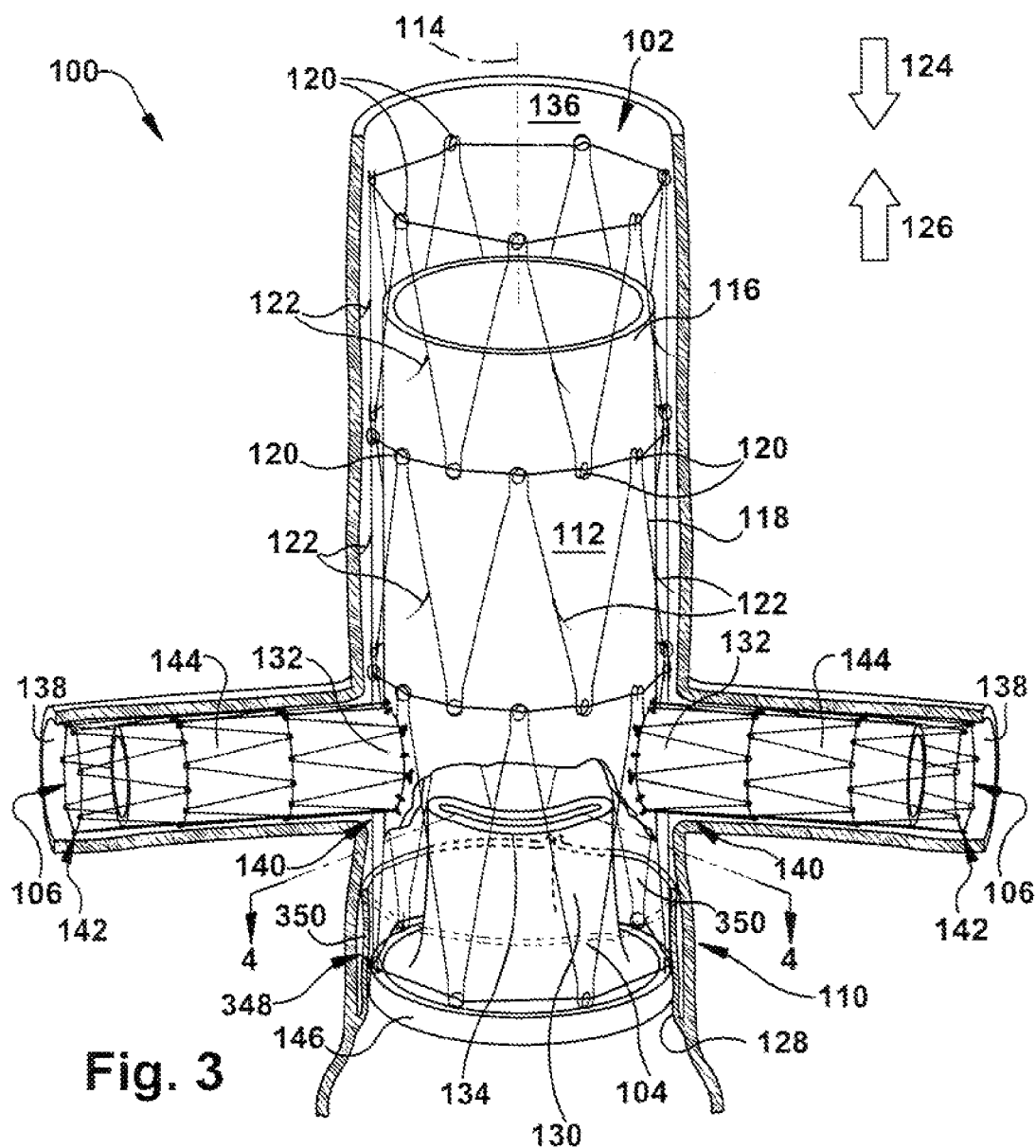
FIG. 3 is a side view of an alternate configuration of the embodiment of FIG. 1.
Figure 4:
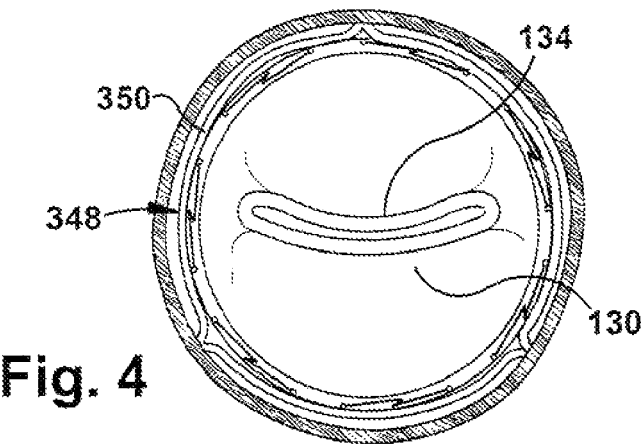
FIG. 4 is a cross-sectional view taken along line 4-4 of FIG. 3.

The native heart valve 348 has at least two native valve leaflets 350, depicted in FIGS. 3 and 4. The native heart valve 348 may be excised, in any suitable manner, before the valve support member 102 is placed in the desired location within the blood vessel of the patient. Alternatively, and as shown in FIGS. 3 and 4, the native valve leaflets 350 may be compressed against an inner wall of the blood vessel of the patient by the valve support member 102. In any case, the native valve leaflets 350 should be rendered inoperative before the apparatus 100 becomes functional.

Once the apparatus 100 is advanced to the desired location, the sheath is retracted to allow the valve support member 102 to expand radially outward into engagement with the aortic wall as shown in the Figures. It should be noted that a balloon (not shown) may be used to assist with the expansion or stabilization of the valve support member 100. Optionally, as the valve support member 102 expands into the aortic wall, the anchor members 122 on the beams 118 of the valve support member embed into the vessel wall to secure the apparatus 100 from migration in the aorta or into the left ventricle.

Once the valve support member 102 is placed within the ascending aorta 136, the branch support member(s) 106 should be placed within the coronary arteries 138. This can be accomplished in a number of different ways, depending upon the structure of the apparatus 100 in general, and the branch support members 106 in particular. One of ordinary skill in the art can readily provide a method for placing the branch support members 106 within the coronary arteries 138 as desired.

For example, the branch support members 106 could be provided separately from the valve support member 102, with each branch support member 106 being threaded, second branch end 142 first, through a coronary opening 132 and a coronary ostia and into the associated coronary artery 138.

As another example of placing the branch support members 106, the first branch ends 140 may be attached to the coronary openings 132, before or after the apparatus is placed within the patient's vasculature, and the branch support members 106 everted with the second branch ends 142 located within the valve member body 112. In this case, each second branch end 142 could pass through the rest of the branch support member 106 and emerge from the first branch end 140, pass through the coronary ostium, and achieve the final placement within the coronary arteries 138.

Yet another method of placing the branch support members 106 involves attaching the first branch ends 140 to the valve support member 102 in the configuration shown in FIGS. 1, 2, and 3 before the apparatus 100 is inserted into the vasculature of the patient. The apparatus 100 may then be manipulated during installation such that the branch support members 106 are folded relatively flat against the valve support member 102 until reaching the desired location for the apparatus. The branch support members 106 may then be maneuvered into the coronary arteries 138 while the valve support member 102 is being positioned as desired within the blood vessel of the patient.

As a final but nonlimiting example, the branch support members 106 may be attached to the valve support member 102 in the configuration shown in FIGS. 1, 2, and 3 before the apparatus 100 is inserted into the vasculature of the patient. The branch support members 106 could then be accordion-folded or telescoped in a direction perpendicular to the longitudinal axis 114 and held in such a collapsed position, optionally at least partially within the valve support member 102. Upon reaching the desired location within the patient's vasculature, the branch support members 106 could be released or manipulated to enter the coronary arteries 138 and assume the position shown in the Figures.

The apparatus 100 and associated methods described above help to protect the lower and/or upper body from elevated venous pressures caused by a diseased tricuspid valve. Problems such as ascites, liver dysfunction, edema and cardiac cirrhosis that are often associated with severe cardiac valve regurgitation can be treated using the apparatus 100 and methods according to the present invention. The apparatus 100 could also be used to bridge the transition between enlarged and normal sections of the aorta. Further, the apparatus 100 and methods of the present invention provide a minimally invasive, endovascular approach to treat severe valvular disease, which is particularly important for high risk patients. This apparatus 100 may be used, for example, with patients who have aortic valve disease or aortic root disease, particularly root aneurysms.

While aspects of the present invention have been particularly shown and described with reference to the preferred embodiment above, it will be understood by those of ordinary skill in the art that various additional embodiments may be contemplated without departing from the spirit and scope of the present invention. For example, the apparatus 100 could be used with any suitable venous or cardiac valves, with appropriate modification to the number, location, and configuration of branch support members 106. A plurality of coronary openings 132 could be provided in the valve support member 102, with less than all of the coronary openings receiving a branch support member 106, to allow for a more-customized fit of the apparatus 100 to the anatomy of a particular patient. The native aortic valve could be approached antegrade, through the left ventricle, rather than the retrograde approach described. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An apparatus for repairing the function of a native aortic valve of a patient, the native aortic valve defining a native valve annulus, the apparatus comprising:
    a tubular valve support member having oppositely disposed first and second valve member ends and a valve member body located between the first and second valve member ends, the valve support member defining a longitudinal axis;
    a prosthetic valve having at least two prosthetic valve leaflets that are coaptable to permit the unidirectional flow of blood, the prosthetic valve being attached to the valve support member adjacent the second valve member end;
    at least two coronary openings in the valve member body located longitudinally adjacent free edges of the at least two prosthetic valve leaflets, at least one of the coronary openings being located so as to be selectively radially aligned with a coronary ostium when the prosthetic valve is located substantially within the native valve annulus; and
    at least two branch support members, each branch support member having first and second branch ends;
    each first branch end of a branch support member being attachable to a coronary opening with the corresponding second branch end of the branch support member extending radially away from the valve support member and through a coronary ostium.

2. The apparatus of claim 1, wherein at least one branch support member is formed integrally with the valve support member.

3. The apparatus of claim 1, wherein at least one branch support member is attached to the valve support member after the valve support member has been placed into a blood vessel of the patient.

4. The apparatus of claim 1, wherein at least one branch support member extends away from the valve support member in a direction perpendicular to the longitudinal axis.

5. The apparatus of claim 1, including at least one anchor member attached to the valve support member and resisting movement of the device in a first longitudinal direction within a blood vessel of the patient.

6. The apparatus of claim 5, including at least one anchor member attached to the valve support member and resisting movement of the device in a second longitudinal direction, opposite the first longitudinal direction, within the blood vessel of the patient.

7. The apparatus of claim 1, including a cushioning cuff attached to at least one of the first and second valve member ends and the second branch end.

8. The apparatus of claim 1, wherein the native heart valve is excised before the valve support member is placed within a blood vessel of the patient.

9. The apparatus of claim 1, wherein the native valve includes at least two native valve leaflets, and the native valve leaflets are compressed against an inner wall of a blood vessel of the patient by the valve support member.

10. The apparatus of claim 1, wherein the valve support member is at least partially lined with a valve support member graft.

11. The apparatus of claim 1, wherein at least one branch support member is at least partially lined with a branch support member graft.

* * * * *